United States Patent
Reever

(10) Patent No.: US 7,485,151 B2
(45) Date of Patent: *Feb. 3, 2009

(54) DELIVERING AN AGENT TO A PATIENT'S BODY

(75) Inventor: Kenneth P. Reever, Hopedale, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 349 days.

This patent is subject to a terminal disclaimer.

(21) Appl. No.: 10/736,493

(22) Filed: Dec. 15, 2003

(65) Prior Publication Data

US 2004/0127996 A1 Jul. 1, 2004

Related U.S. Application Data

(62) Division of application No. 09/855,566, filed on May 15, 2001, now Pat. No. 6,685,745.

(51) Int. Cl.
*A61F 2/04* (2006.01)

(52) U.S. Cl. .............. 623/23.7; 623/23.66; 623/23.71

(58) Field of Classification Search ............ 623/23.7, 623/23.66
See application file for complete search history.

(56) References Cited

U.S. PATENT DOCUMENTS

| | | | |
|---|---|---|---|
| 3,811,450 A | 5/1974 | Lord | |
| 3,923,066 A | 12/1975 | Francisoud et al. | |
| 4,026,296 A | 5/1977 | Stoy et al. | |
| 4,307,723 A | 12/1981 | Finney | |
| 4,655,771 A | 4/1987 | Wallsten | |
| 4,713,049 A | 12/1987 | Carter | |
| 4,732,152 A | 3/1988 | Wallsten et al. | |
| 4,842,597 A | 6/1989 | Brook | |
| 4,931,037 A | 6/1990 | Wetterman | |
| 4,954,126 A | 9/1990 | Wallsten | |

(Continued)

FOREIGN PATENT DOCUMENTS

EP 0 467 516 A1 1/1992

(Continued)

OTHER PUBLICATIONS

International Search Report for PCT/US02/14704.

(Continued)

*Primary Examiner*—Dave Willse
*Assistant Examiner*—Javier G. Blanco
(74) *Attorney, Agent, or Firm*—Cooley Godward Kronish LLP

(57) ABSTRACT

A medical stent provides an active agent to a patient's body while simultaneously maintaining an open passageway within the body of the patient. The stent includes a first segment, a second segment, a connecting segment disposed between the first and second segments, and the active agent. The active agent may be a hemostatic agent that stops or controls bleeding by coagulation, or any other medical drug, such as, for example an antibiotic or an anticoagulant. When the stent is properly positioned within the patient's urinary system, the first segment is located on one side of the external sphincter and the second segment is located on the other side. The connecting segment is sized to extend through the external sphincter to couple the first and second segments together while not interfering with the normal operation of the external sphincter.

19 Claims, 16 Drawing Sheets

U.S. PATENT DOCUMENTS

| | | | |
|---|---|---|---|
| 4,955,859 A | 9/1990 | Zilber | |
| 4,973,301 A | 11/1990 | Nissenkorn | |
| 4,978,341 A | 12/1990 | Niederhauser | |
| 4,994,066 A | 2/1991 | Voss | |
| 4,995,868 A | 2/1991 | Brazier | |
| 5,026,377 A | 6/1991 | Burton et al. | |
| 5,041,092 A | 8/1991 | Barwick | |
| 5,059,169 A | 10/1991 | Zilber | |
| 5,061,275 A | 10/1991 | Wallsten et al. | |
| 5,078,720 A | 1/1992 | Burton et al. | |
| 5,116,309 A | 5/1992 | Coll | |
| 5,147,370 A | 9/1992 | McNamara et al. | |
| 5,167,614 A | 12/1992 | Tessmann et al. | |
| 5,207,672 A | 5/1993 | Roth et al. | |
| 5,220,927 A | 6/1993 | Astrahan et al. | |
| 5,221,253 A | 6/1993 | Coll | |
| 5,224,953 A | 7/1993 | Morgentaler | |
| 5,246,445 A | 9/1993 | Yachia et al. | |
| 5,282,823 A | 2/1994 | Schwartz et al. | |
| 5,290,271 A * | 3/1994 | Jernberg | 604/891.1 |
| 5,300,022 A | 4/1994 | Klapper et al. | |
| 5,346,467 A | 9/1994 | Coll | |
| 5,352,198 A | 10/1994 | Goldenberg et al. | |
| 5,354,263 A | 10/1994 | Coll | |
| 5,354,309 A | 10/1994 | Schnepp-Pesch et al. | |
| 5,356,423 A | 10/1994 | Tihon et al. | |
| 5,364,340 A | 11/1994 | Coll | |
| 5,372,600 A | 12/1994 | Beyar et al. | |
| 5,380,299 A | 1/1995 | Fearnot et al. | |
| 5,383,928 A | 1/1995 | Scott et al. | |
| 5,391,196 A | 2/1995 | Devonec | |
| 5,464,650 A | 11/1995 | Berg et al. | |
| 5,514,178 A | 5/1996 | Torchio | |
| 5,520,697 A | 5/1996 | Lindenberg et al. | |
| 5,540,713 A | 7/1996 | Schnepp-Pesch et al. | |
| 5,571,166 A | 11/1996 | Dinh et al. | |
| 5,614,204 A | 3/1997 | Cochrum | |
| 5,637,087 A | 6/1997 | O'Neil et al. | |
| 5,637,113 A | 6/1997 | Tartaglia et al. | |
| 5,649,977 A | 7/1997 | Campbell | |
| 5,667,486 A | 9/1997 | Mikulich et al. | |
| 5,674,241 A | 10/1997 | Bley et al. | |
| 5,697,967 A | 12/1997 | Dinh et al. | |
| 5,700,286 A | 12/1997 | Tartaglia et al. | |
| 5,702,361 A | 12/1997 | Evans et al. | |
| 5,707,386 A | 1/1998 | Schnepp-Pesch et al. | |
| 5,722,984 A | 3/1998 | Fischell et al. | |
| 5,728,068 A | 3/1998 | Leone et al. | |
| 5,766,209 A | 6/1998 | Devonec | |
| 5,776,161 A | 7/1998 | Globerman | |
| 5,779,732 A | 7/1998 | Amundson | |
| 5,788,979 A | 8/1998 | Alt et al. | |
| 5,792,400 A | 8/1998 | Talja et al. | |
| 5,817,102 A | 10/1998 | Johnson et al. | |
| 5,824,049 A | 10/1998 | Ragheb et al. | |
| 5,830,179 A | 11/1998 | Mikus et al. | |
| 5,833,651 A | 11/1998 | Donovan et al. | |
| 5,833,707 A | 11/1998 | McIntyre et al. | |
| 5,837,313 A | 11/1998 | Ding et al. | |
| 5,851,231 A | 12/1998 | Wolff et al. | |
| 5,860,999 A | 1/1999 | Schnepp-Pesch et al. | |
| 5,865,815 A | 2/1999 | Tihon | |
| 5,869,127 A | 2/1999 | Zhong | |
| 5,873,904 A | 2/1999 | Ragheb et al. | |
| 5,876,417 A | 3/1999 | Devonec et al. | |
| 5,882,335 A | 3/1999 | Leone et al. | |
| 5,908,054 A | 6/1999 | Safabash et al. | |
| 5,916,195 A | 6/1999 | Eshel et al. | |
| 5,925,683 A | 7/1999 | Park | |
| 5,928,208 A | 7/1999 | Chu et al. | |
| 5,928,217 A | 7/1999 | Mikus et al. | |
| 5,964,771 A | 10/1999 | Beyar et al. | |
| 5,980,550 A | 11/1999 | Eder et al. | |
| 5,993,445 A | 11/1999 | Issa | |
| 5,997,468 A | 12/1999 | Wolff et al. | |
| 6,017,977 A | 1/2000 | Evans et al. | |
| 6,022,312 A | 2/2000 | Chaussy et al. | |
| 6,022,334 A | 2/2000 | Edwards et al. | |
| 6,033,413 A | 3/2000 | Mikus et al. | |
| 6,053,900 A | 4/2000 | Brown et al. | |
| 6,071,305 A | 6/2000 | Brown et al. | |
| 6,080,190 A | 6/2000 | Schwartz | |
| 6,096,070 A | 8/2000 | Ragheb et al. | |
| 6,099,562 A | 8/2000 | Ding et al. | |
| 6,099,563 A | 8/2000 | Zhong | |
| 6,120,536 A | 9/2000 | Ding et al. | |
| 6,139,536 A | 10/2000 | Mikus et al. | |
| 6,146,373 A | 11/2000 | Cragg et al. | |
| 6,152,943 A | 11/2000 | Sawhney | |
| 6,160,025 A | 12/2000 | Slaikeu et al. | |
| 6,187,370 B1 | 2/2001 | Dinh et al. | |
| 6,290,666 B1 | 9/2001 | Devonec | |
| 6,338,739 B1 * | 1/2002 | Datta et al. | 623/1.15 |
| 6,423,050 B1 | 7/2002 | Twardowski | |
| 6,494,908 B1 | 12/2002 | Huxel et al. | |
| 6,682,555 B2 * | 1/2004 | Cioanta et al. | 623/1.21 |
| 6,685,745 B2 | 2/2004 | Reever | |
| 2002/0055787 A1 | 5/2002 | Lennox et al. | |
| 2002/0128705 A1 | 9/2002 | Devonec et al. | |
| 2003/0199988 A1 | 10/2003 | Devonec et al. | |
| 2006/0122709 A1 | 6/2006 | Devonec | |

FOREIGN PATENT DOCUMENTS

| | | |
|---|---|---|
| EP | 0 684 802 B1 | 12/1995 |
| EP | 0 547 530 | 9/1996 |
| EP | 0 935 977 A3 | 8/1999 |
| FR | 2 767 673 A1 | 3/1999 |
| WO | 91/12779 | 9/1991 |
| WO | WO94/18907 | 9/1994 |
| WO | 96/02210 | 2/1996 |
| WO | 97/37717 | 10/1997 |
| WO | 99/23952 | 5/1999 |

OTHER PUBLICATIONS

The Merck Index, 12th Edition, Susan Budavari, Editor, THER-8, 17, 23, and 27, Merck Research Laboratories, Whitehouse Station, NJ. (1996).

Soni et al., "Use of Memokath, s Second Generation Urethral Stent for Relief of Urinary Retention in Male Spinal Cord Injured Patients," *Paraplegia*, 32:480-488 (1994).

* cited by examiner

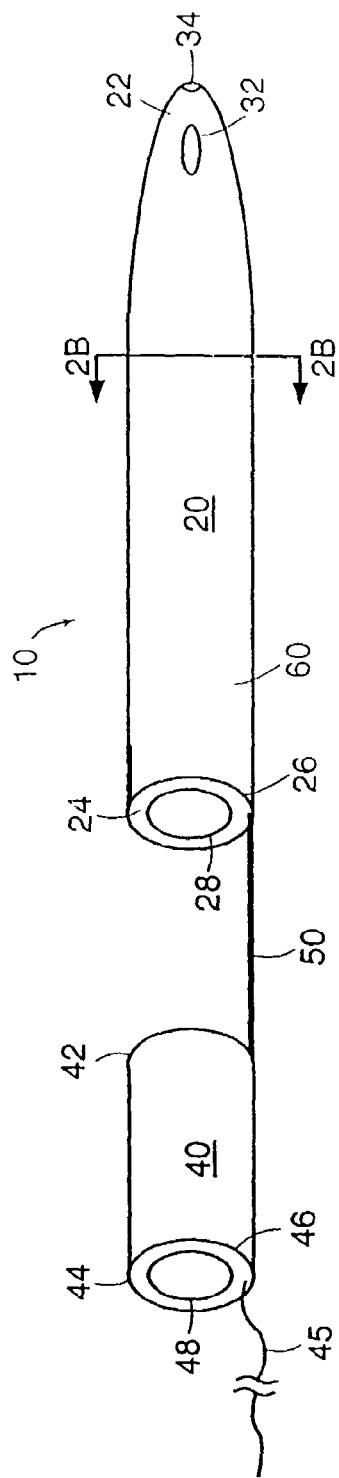
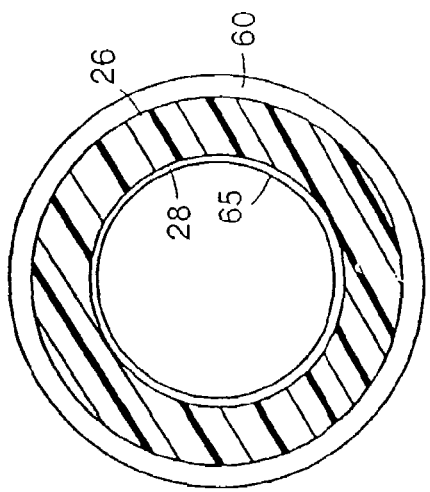
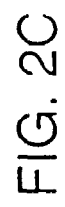

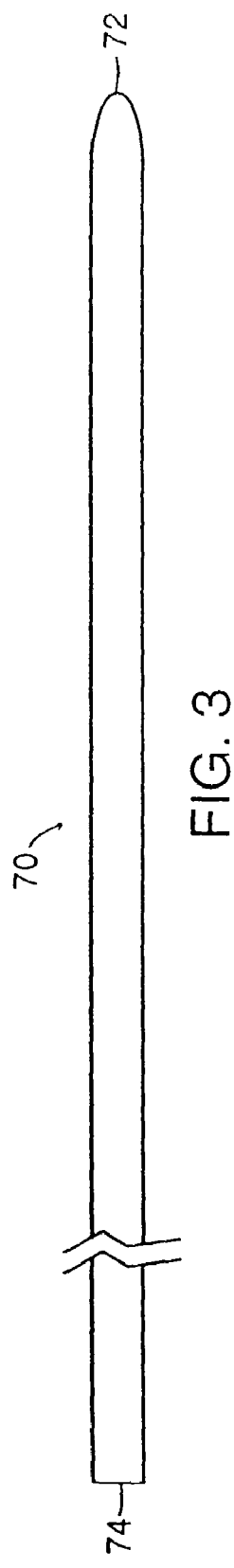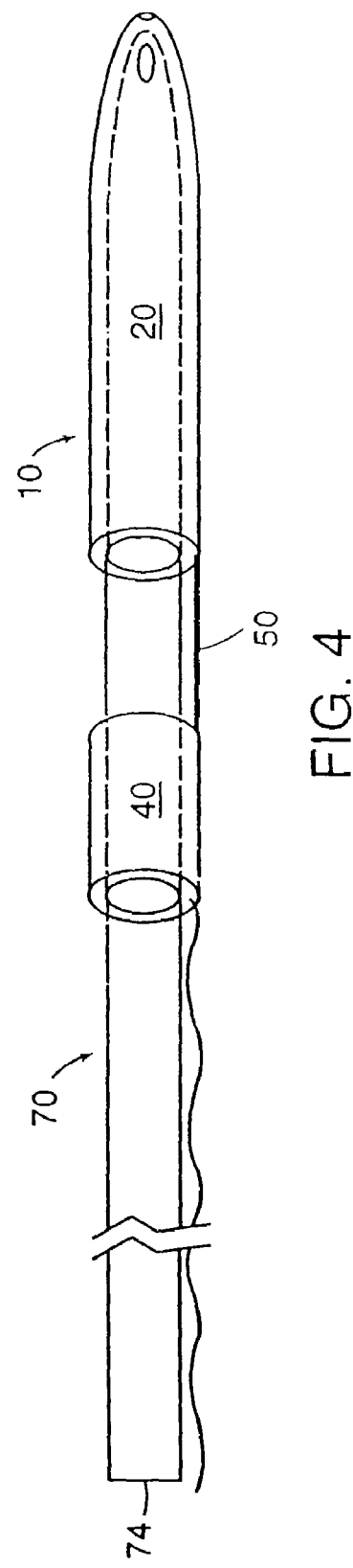

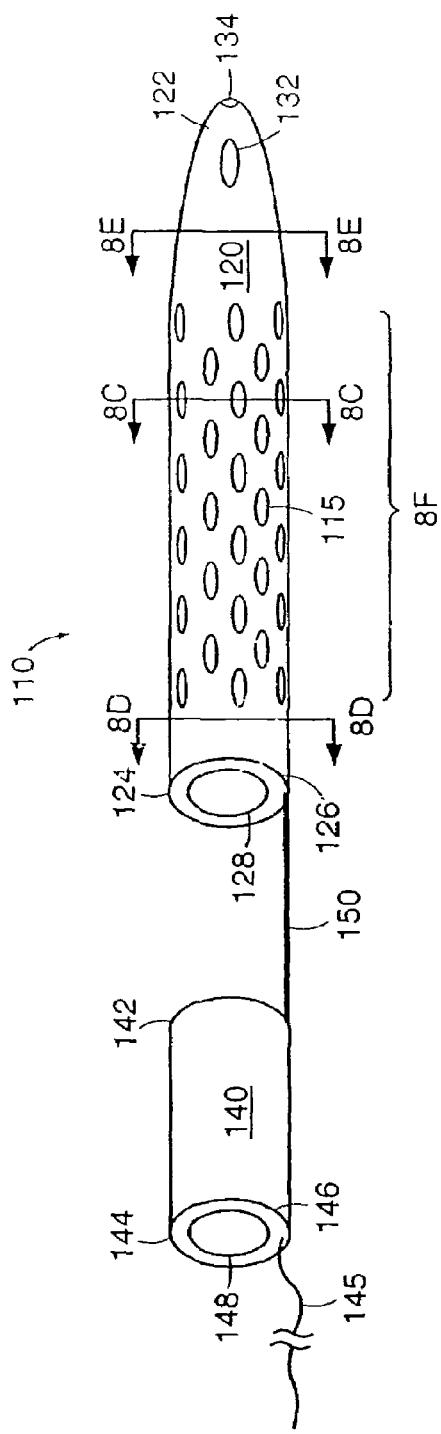
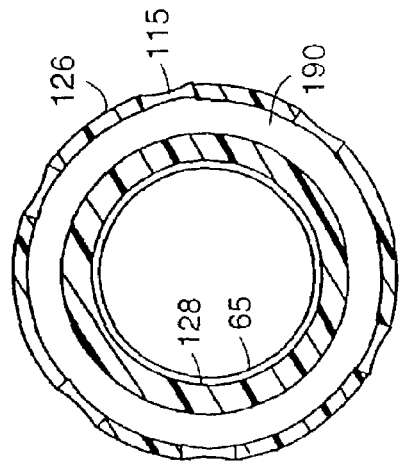
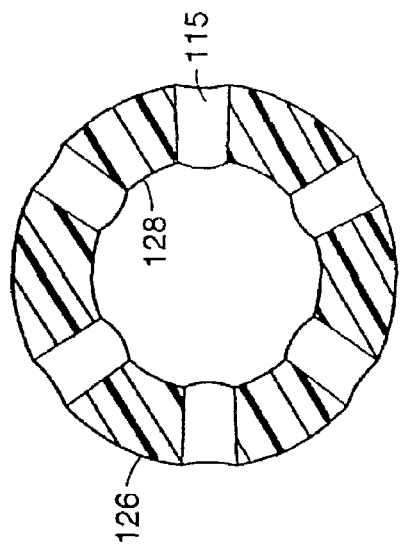
FIG. 8A
FIG. 8B
FIG. 8C

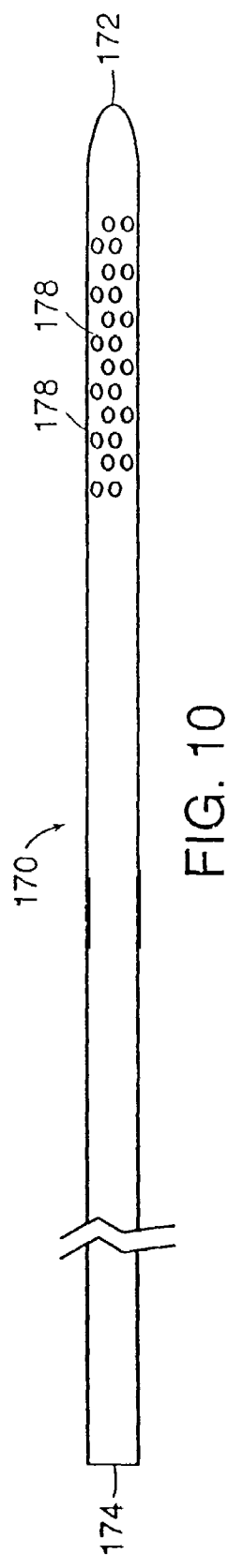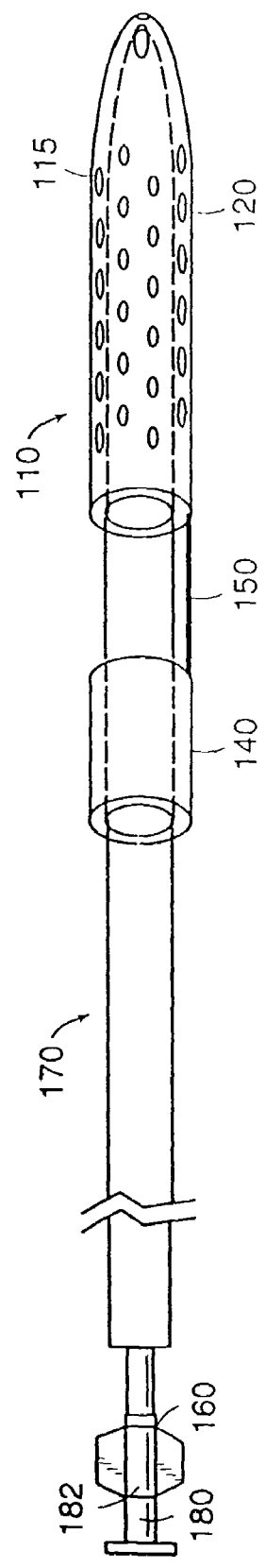
FIG. 10
FIG. 11

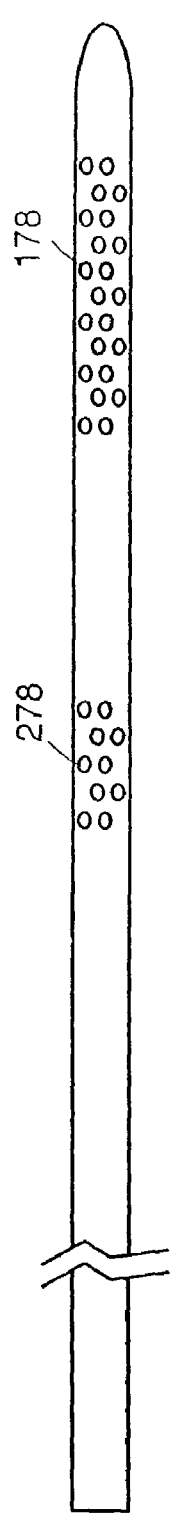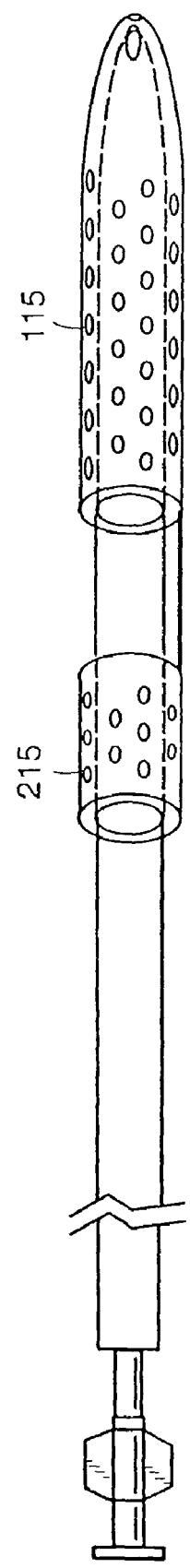
FIG. 14A
FIG. 14B

DELIVERING AN AGENT TO A PATIENT'S BODY

CROSS-REFERENCE TO RELATED APPLICATIONS

This patent application is a divisional of U.S. patent application Ser. No. 09/855,566, filed May 15, 2001, now U.S. Pat. No. 6,685,745, the entire disclosure of which is incorporated by reference herein.

TECHNICAL FIELD

This invention relates generally to devices and methods for delivering an agent, such as a hemostatic agent, to a body lumen or cavity.

BACKGROUND INFORMATION

The prostate is a gland in the male urinary system located directly below the bladder and surrounding the urethra. A common urological disorder that some men encounter is enlargement of the prostate due to disease or decreases in hormone production. Generally, the enlarged prostate tends to constrict the-urethra resulting in reduced urination flow and/or urine retention.

A medical professional has a number of options to treat a patient suffering from retention caused by the enlargement of the patient's prostate. One option is to perform a surgical procedure that cuts or removes parts of the patient's diseased prostatic tissue (the enlarged section of the prostate). Another option is to insert a device, such as, for example, a stent to facilitate drainage of urine and/or blood from the patient's bladder and urethra.

SUMMARY OF THE INVENTION

The invention involves controlling bleeding associated with the insertion of medical devices (such as stents) and/or surgical procedures that involve cutting of tissue. The present invention generally relates to stents that are able to deliver a hemostatic agent during or after the insertion of the stent. By preventing bleeding in the tissues surrounding the stent, obstruction or other problems that can occur when the blood coagulates inside or around the stent are reduced or avoided.

In one aspect, the invention relates to a prostatic stent. The prostatic stent is used to maintain an open passageway from a patient's bladder through the urethra and to deliver an agent to tissue within the patient's urinary system. The prostatic stent includes a first segment, a second segment, a connecting segment, and the agent. The first and second segments can be tubular members disposed on either side of the patient's external sphincter and connected together by the connecting segment. The first segment includes an external surface coated with the agent, an internal surface, a distal end, a proximal portion, and a lumen defined by the internal surface and extending within the first segment. (The directional terms distal and proximal require a point of reference. Herein, the reference point in determining direction is in the perspective of the patient. Therefore, the term distal herein refers to a direction that points out of the patient's body, and the term proximal refers to the direction that points into the patient's body.) The proximal portion includes at least one opening in communication with the lumen for draining fluid from the patient's bladder. The second segment includes an external surface, an internal surface, a distal end, a proximal end, and a lumen defined by the internal surface and extending within the second segment. The connecting segment is a thin flexible member adapted to extend through an opening within the patient's external sphincter without interfering with the normal function of the external sphincter. When the prostatic stent is placed with the patient's body, the first segment is located on the proximal side of the patient's external sphincter, the second segment is located on the distal side of the patient's external sphincter, and the connecting segment extends between the first and second segment within the external sphincter.

Embodiments of this aspect of the invention can include the following features. The agent on the external surface of the first segment may be a hemostatic agent that controls or stops bleeding within a tissue. The hemostatic agent may be in the form of a powder, a liquid, a gel, or a fibrous matrix embedded within a biodegradable polymer. The external surface of the second segment may also be coated with the hemostatic agent. The internal surfaces of the first and second segments may be coated with an anticoagulant agent that prevents blood from coagulating and thus occluding the lumens of the first and second segments. The prostatic stent may further include a suture or other thin flexible member attached to the distal end of the second segment. The suture should be long enough to extend from the distal end of the second segment through the patient's urethra and terminate in close proximity to the meatus.

In general, in another aspect, the invention relates to a method of placing the prostatic stent within a patient's urinary system. A medical professional inserts and positions the prostatic stent with the aid of a stylet. The stylet includes a proximal end and a distal end and is sized to fit within the lumens of the first and second segments of the prostatic stent. Prior to inserting the prostatic stent, the medical professional passes the stylet through the lumens of the second and first segments, thereby removably connecting the prostatic stent to the stylet. The medical professional then inserts and advances the prostatic stent until the proximal portion of the first segment is located within the bladder of the patient. When properly positioned, the first segment of the prostatic stent is located on the proximal side of the external sphincter, the second segment is located on the distal side of the external sphincter, and the connecting segment extends through the external sphincter. Once the prostatic stent is properly positioned, the medical professional removes the stylet from the prostatic stent and from the patient's urethra, thereby leaving the prostatic stent to remain positioned within the patient's urinary system. The agent, which is on the external surface of the first segment, is transferred to the tissue of the urethra during insertion and after placement of the prostatic stent. The prostatic stent may be removed from the patient's body at some later time by simply pulling on the suture or through endoscopic means.

In general, in another aspect, the invention relates to a prostatic stent that includes ports adapted to delivering an agent to the prostatic stent. The prostatic stent includes a first segment, a second segment, and a connecting segment. The first and second segments are tubular members disposed on either side of the patient's external sphincter and are connected together by the connecting segment. The first segment includes an external surface, an internal surface, a distal end, a proximal portion, a lumen defined by the internal surface and extending within the first segment, and a plurality of ports for conveying the agent to the external surface of the first segment. The proximal portion includes at least one opening in communication with the lumen for draining fluid from the patient's bladder. The second segment includes an external surface, an internal surface, a distal end, a proximal end, and a lumen defined by the internal surface and extending within the second segment. The connecting segment is a thin flexible member adapted to extend through an opening within the patient's external sphincter without interfering with the normal function of the external sphincter. When the prostatic stent is placed within a patient's body, the first segment is located on the proximal side of the patient's external sphincter, the second segment is located on the distal side of the patient's external sphincter, and the connecting segment extends between the first and second segment within the external sphincter.

Embodiments of this aspect of the invention can include the following features. The internal surfaces of the first and second segments may be coated with an anticoagulant agent that prevents blood from coagulating and thus occluding the lumens of the first and second segments. The second segment may include a plurality of ports for conveying the agent to the external surface of the second segment. The prostatic stent may further include a suture or other thin flexible member attached to the distal end of the second segment. The suture should be long enough to extend from the distal end of the second segment through the patient's urethra and terminate in close proximity to the meatus.

The agent to be delivered to the prostatic stent may be a hemostatic agent or other drug, and may be in the form of a liquid, gel, or powder. The agent may also be formed from a two component formulation such as, for example, combining a polymerizing agent with a polymerizable agent. In some embodiments, the agent is discharged to the prostatic stent during insertion to treat the entire urethra. In other embodiments, treatment is concentrated to a specific region of the patient's urethra and therefore, the agent is discharged after placement of the prostatic stent within the patient's prostatic urethra.

In general, in another aspect, the invention relates to a method of placing the prostatic stent within a patient's urinary system and delivering an agent to the prostatic stent in vivo. A medical professional inserts and positions the prostatic stent with the aid of a stylet. The stylet includes a proximal end, a distal end, a fluid channel for conveying the agent, and a plurality of openings in fluid communication with the fluid channel. The stylet is sized to fit within the lumens of the first and second segments of the prostatic stent, and the plurality of openings on the stylet are sized and positioned to communicate with the plurality of ports within the first segment of the prostatic stent when the stylet and stent are connected. Prior to inserting the prostatic stent, the medical professional passes the stylet through the lumens of the second and first segments and aligns the plurality of openings on the stylet with the plurality of ports on the prostatic stent, thereby creating a continuous pathway for a fluid to flow. Connected to the distal end of the stent is a syringe containing the active agent that is to be delivered to the stent. The medical professional then inserts and advances the prostatic stent and stylet until the proximal portion of the first segment is located within the bladder of the patient. The medical professional may either activate the syringe resulting in the discharge of the agent to the prostatic stent either during insertion or after the prostatic stent has been properly positioned. When properly positioned, the first segment of the prostatic stent is located on the proximal side of the external sphincter, the second segment is located on the distal side of the external sphincter, and the connecting segment extends through the external sphincter. Once the prostatic stent is properly positioned and the agent has been discharged to the prostatic stent, the medical professional removes the stylet from the prostatic stent and from the patient's urethra, thereby leaving the prostatic stent to remain positioned within the patient's urinary system. The prostatic stent may be removed from the patient's body at some later time by simply pulling on the suture or through endoscopic means.

In some embodiments, the stylet may feature a first fluid channel, a second fluid channel, and a fluid mixing channel to accommodate an agent that is formed from a polymerizing agent and a polymerizable agent. The medical professional simultaneously discharges the polymerizing agent into the first fluid channel and the polymerizable agent into the second fluid channel. The polymerizing and polymerizable agents mix together forming the agent in the fluid mixing channel and the agent is then delivered to the plurality of ports in the first segment of the prostatic stent.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 2A is a perspective view of one embodiment of a prostatic stent of the invention.

FIG. 2B is an enlarged cross-sectional view of the prostatic stent view taken along line BB in FIG. 2A.

FIG. 2C is another cross-sectional view of another embodiment of a prostatic stent.

FIG. 3 is a side view of a stylet used to position the prostatic stent of FIG. 2A within the male urinary system.

FIG. 4 is a perspective view of the stylet inserted within the prostatic stent.

FIG. 8A is a perspective view of another embodiment of a prostatic stent.

FIG. 8B is a cross-sectional view of the prostatic stent taken along line CC in FIG. 8A.

FIG. 8C is another cross-sectional view taken along line CC of another embodiment of a prostatic stent.

FIG. 10 is a side view of the stylet.

FIG. 11 is a perspective view of the stylet connected to the prostatic stent of FIG. 8A.

FIG. 14A is a side view of another embodiment of a stylet.

FIG. 14B is a perspective view of the stylet according to FIG. 14A connected to a prostatic stent.

DESCRIPTION

Figure 1:
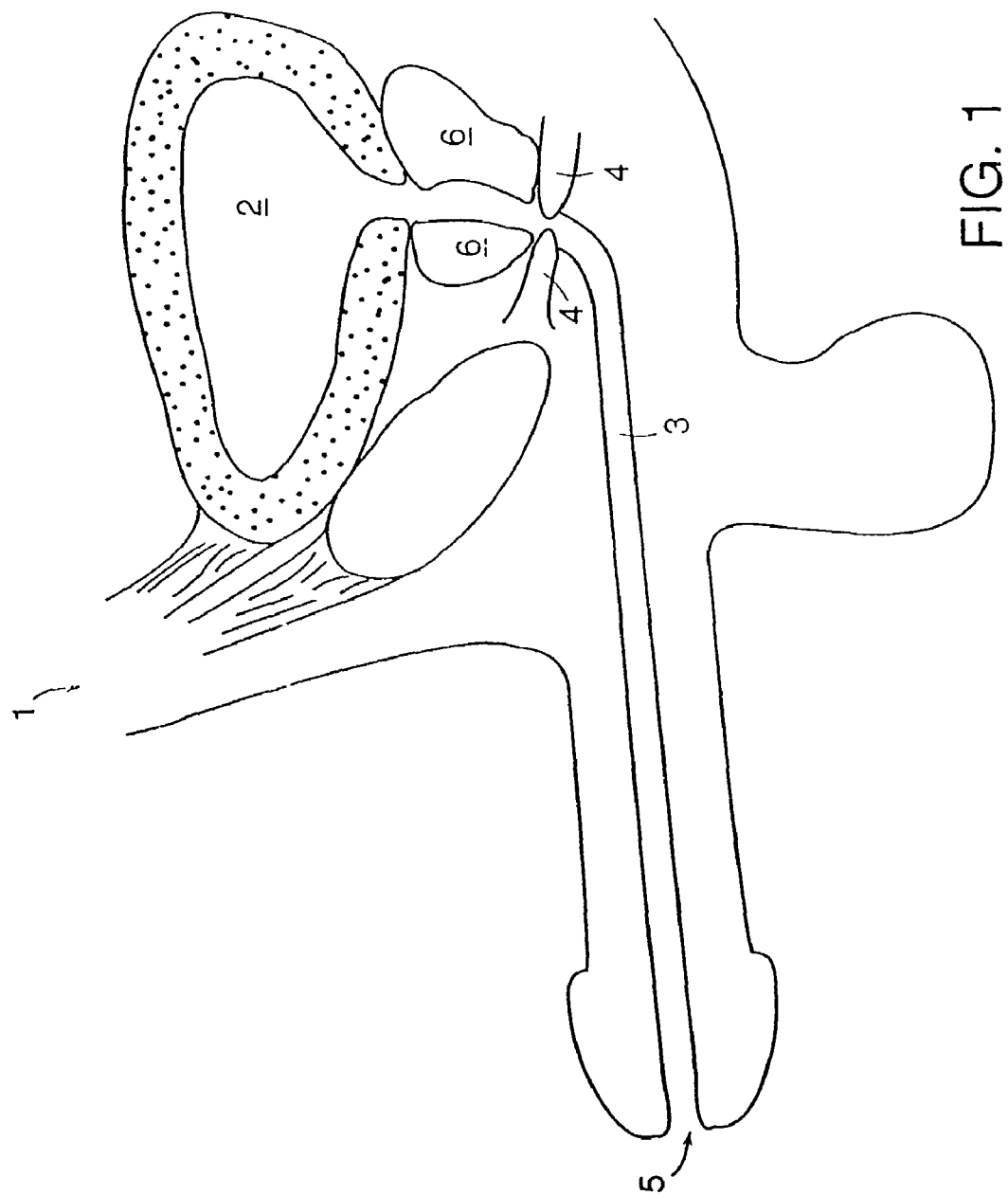
FIG. 1 is a schematic view of a male urinary system.

Bleeding and/or hemorrhaging can result from surgical and/or other medical procedures designed to eliminate constriction or obstruction of a male patient's urinary system 1. For reference, FIG. 1 shows an illustration of the male urinary system 1, which includes a bladder 2, a urethra 3, an external sphincter 4, and a meatus 5. The male urinary system 1 may become obstructed when, the patient's prostate 6 enlarges due to disease or a decrease in hormone production. The enlarged prostate 6 constricts the section of the urethra 3 that it surrounds, commonly referred to as the prostatic urethra and causes urine retention. One of the objects of the present invention is to maintain an open passageway free of debris and bleeding from the patient's bladder through the urethra while simultaneously preserving the patient's voluntary control over urination by allowing the external sphincter 4 to open and close under patient control.

Although coating a prostatic stent, such as the Trestle™ available from Boston Scientific Corporation of Natick, Mass., with an agent, such as a hemostatic agent, is described in some detail herein, other urethral medical devices, such as, for example, urethral catheters, specifically Foley catheters, may also be similarly coated and fall within the scope of the invention. Such urethral catheters are flexible tubes that have a length sufficient to extend from the bladder through the urethra to a collection bag located outside of a patient's body. Urethral catheters may have retention devices extending from their proximal ends to anchor these catheters within the patient's bladder. Typically, urethral catheters are used to provide patients with constant urine drainage from the bladder when normal urination is disrupted by, for example, an infection, an enlarged prostate, or injury.

Referring to FIG. 2A, a prostatic stent 10 comprises a first segment 20, a second segment 40, a connecting segment 50 disposed between the first and second segments 20, 40, and a hemostatic agent 60. The prostatic stent 10 is sized such that when the prostatic stent 10 is properly positioned within the urethra 3 of a patient, the first segment 20 is located substantially within the patient's prostatic urethra (on the proximal side of the patient's external sphincter), the second segment 40 is located within the bulbar urethra (on the distal side of the external sphincter), and the connecting segment 50 is located within the external sphincter. To stop or control bleeding within the patient's urethra 3, the prostatic stent 10 is coated with the hemostatic agent 60.

The first and second segments 20, 40 are tubular members made from biocompatible materials that are sufficiently flexible to conform to the shape of the patient's urethra 3 while simultaneously are also sufficiently rigid to maintain an open passageway through the urethra 3. In the disclosed embodiment, the first and second segments 20, 40 have a circular cross-sectional shape. Alternatively, the segments 20, 40 could have a triangular, elliptical, rectangular or even square cross-sectional shape. Extending within each one of the segments 20, 40 is a lumen for draining bodily fluids, such as urine or blood, from the bladder 2 of the patient.

Specifically, the first segment 20 has a proximal portion 22, a distal end 24, an external surface 26 and an internal surface 28 that defines the lumen of the first segment 20. The proximal portion 22 has at least one opening 32 in fluid communication with the lumen of the first segment 20 for receiving bodily fluids from the bladder 2 and may have a proximal opening 34 sized to receive a guide wire.

Either prior to or after insertion in a patient's body, the multi-segment prostatic stent 10 (e.g., the Trestle™), or other urethral catheter, can have its external surface coated with a hemostatic agent 60. In one disclosed embodiment, prior to insertion of the prostatic stent 10 into the patient's urethra 3, the external surface 26 of the first segment 20 is coated with a hemostatic agent 60 to control or to stop bleeding within the tissue of the urethra 3. The coated external surface 26 contacts the tissue of the patient's urethra 3 when the prostatic stent 10 is located properly within the patient's body. The hemostatic agent 60 may be any agent that stops bleeding by coagulation such as, for example, but not limited to thrombin, fibrin, algin, collagen, and combination thereof. The hemostatic agent 60 may be in the form of a liquid, a powder, a gel or a fibrous matrix, and maybe combined with a bioabsorbable polymer that delivers the hemostatic agent 60 to the urethral tissue at timed intervals. FIG. 2B shows a cross-sectional view taken along line BB in FIG. 2A of one embodiment of the prostatic stent 10. Similarly, the internal surface 28 of the first segment 20 can be pre-coated with an anticoagulant agent 65 such as heparin, to prevent blood from coagulating and thus to prevent occlusion of the lumen of the first segment 20, as shown in FIG. 2C. Other suitable anticoagulants include, but are not limited to, acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, hirudin, lyapolate sodium, oxazidione, pentosan polysulfate, phenindione, phenprocoumon, phosvitin, picotamide, tioclomarol and warfarin. An anticoagulant may also include antithrombotic agents such as, for example, but are not limited to argatroban, cilostazol, clopidogrel, cloricromen, dalteparin, daltroban, defibrotide, enoxaparin, indobufen, iloprost, integrelin, isbogrel, lamifiban, lamoparin, nadroparin, ozagrel, picotamide, plafibride, reviparin sodium, ridogrel, sulfin pyrazone, taprostene, ticlopidine, tinzaparin, tirofiban, and triflusal (see THE MERCK INDEX, Ther-8 (Susan Budavari et al. eds., $12^{th}$ ed. 1996)). Also considered to have anticoagulant properties are thrombolytic agents, such as, for example, anistreplase, plasmin, pro-urokinase, streptokinase, tissue plasminogen activator, or urokinase (see THE MERCK INDEX, Ther-27 (Susan Budavari et al. eds., $12^{th}$ ed. 1996)).

The second segment 40 includes a proximal end 42, a distal end 44, an external surface 46, and an internal surface 48 that defines the lumen extending within the second segment 40. In the disclosed embodiment, the external surface 46 is not coated with the hemostatic agent 60, however in alternative embodiments the second segment 40 may include a hemostatic agent 60 on the external surface 46 if desired. Extending from the distal end of the second segment 40 is a removal segment 45. The removal segment 45 is a long thin flexible element that extends from the distal end 44 of the second segment 40 and terminates outside of the patient's body when the prostatic stent 10 is properly positioned within the patient's urinary system 1. The removal segment 45 is a useful tool to the medical professional during the placement and the removal of the prostatic stent 10. During placement of the prostatic stent 10, the medical professional restrains the portion of the removal segment 45 that remains outside of the patient's body to ensure that the first and second segments 20, 40 are separated and the connecting segment 50 does not buckle. To remove the prostatic stent 10, the medical professional simply pulls on the removal segment 45 to dislodge the prostatic stent 10 from its placement within the patient's body.

The connecting segment 50 is a thin element that is intended to extend through the patient's external sphincter 4 to couple the first and second segments 20, 40 together, while not interfering with the normal operation of the external sphincter 4. In the disclosed embodiment, the connecting segment 50 is a thin stainless steel wire coated in silicone. The connecting segment 50 can also be made from other biocompatible metals such as titanium, for example, or from a thin strip of a biocompatible polymer or a suture. Alternatively, the connecting segment 50 may include a plurality of sutures or even a continuous pliable tube that is compressible by the external sphincter 4.

To position properly the prostatic stent 10 with the patient's urinary system 1, the medical professional uses a stylet 70 for pushing the prostatic stent 10 through the patient's urethra 3. One embodiment of the stylet 70 is shown in FIG. 3. The stylet 70 has a proximal end 72 and a distal end 74, and is sized to fit within the lumens of the first and second segments 20, 40. The stylet 70 is made from any biocompatible material that is sufficiently flexible to be able to navigate around natural bends in the patient's anatomy, while simultaneously sufficiently rigid to push the prostatic stent 10 through the patient's urethra 3.

Figure 5:
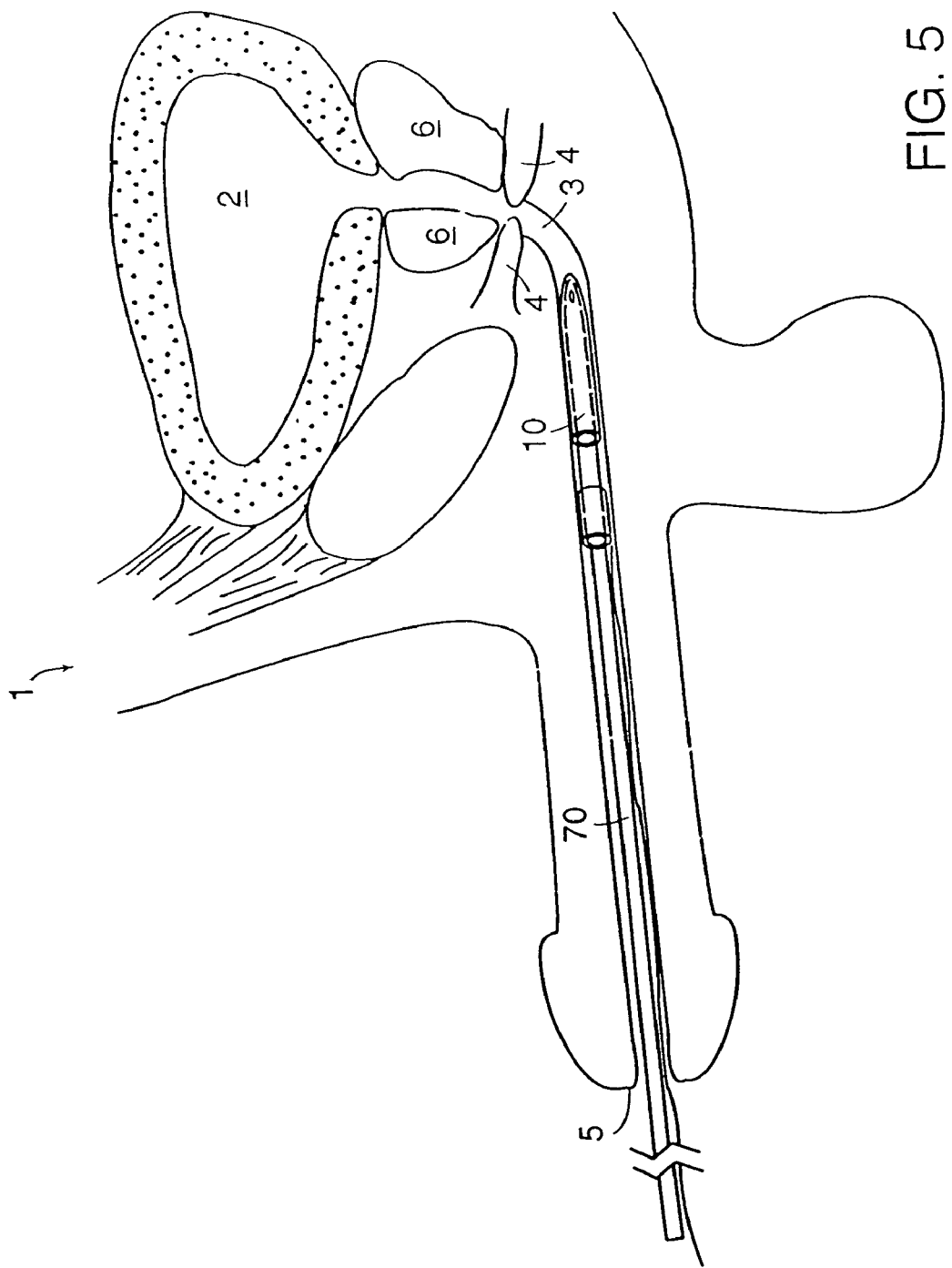
FIG. 5 is a schematic view of the stylet and prostatic stent being inserted into the male urinary system.
Figure 6:
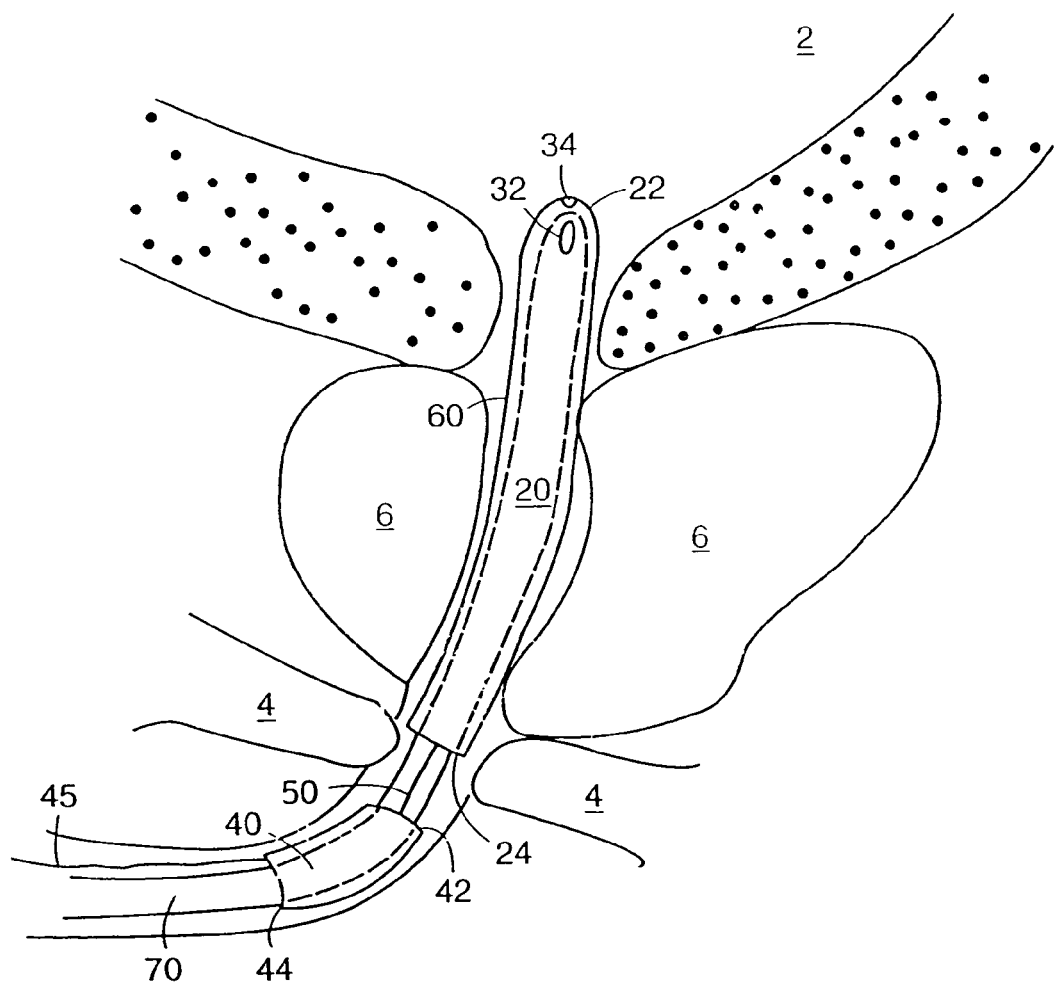
FIG. 6 is an enlarged schematic view of the stylet and prostatic stent during placement within the male urinary system.

Referring to FIG. 4, the medical professional passes the stylet 70 through the lumens of the second and first segments 40, 20, thereby connecting the stylet 70 to the prostatic stent 10. The medical professional then inserts the prostatic stent 10 and stylet 70 into the patient's meatus 5 as shown in FIG. 5 and navigates the prostatic stent 10 to its proper position (see FIG. 6) such that the distal end 24 of the first segment 20 is on the proximal side of the external sphincter 4, the proximal end 42 of the second segment 40 is on the distal side of the external sphincter 4, and the connecting segment 50 extends between the first and second segments 20, 40 within the external sphincter 4. The first segment 20 is now located substantially within the patient's prostatic urethra with its proximal portion 22 located within the patient's bladder 2 and the external surface 26 of the first segment 20 in contact with the diseased prostatic tissue (prostate 6). The diseased prostatic tissue absorbs the hemostatic agent 60 located on the external surface 26 of the first segment 20. The hemostatic agent 60 on the external surface 26 of the first segment 20 causes the coagulation of any blood in the area and therefore controls or stops excessive bleeding in the prostatic urethra which may occur due to the insertion of the prostatic stent 10 or from prior surgical procedures. Alternatively, the hemostatic agent 60 may be replaced prior to insertion with another medical agent or drug for other treatments of the diseased prostatic tissue, such as, for example, an antibiotic.

Figure 7:
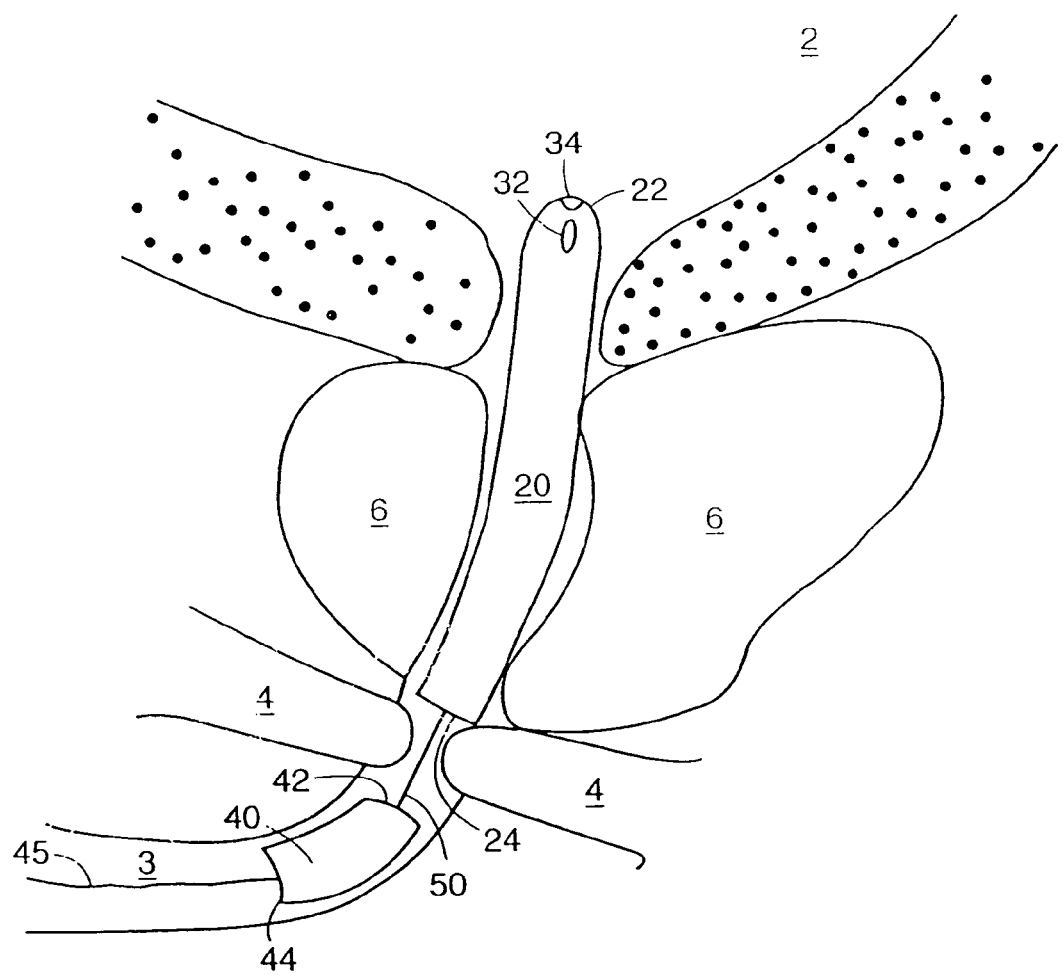
FIG. 7 is another enlarged schematic view showing the proper placement of the prostatic stent within the male urinary system.

Referring to FIG. 7, after the medical professional confirms proper placement of the prostatic stent 10 through radiological means, he or she removes the stylet 70 from the prostatic stent 10, thereby leaving the prostatic stent 10 positioned within the patient's urinary system 1. With the stylet 70 removed the patient regains use of his external sphincter 4 such that the patient has control over bladder voiding. Any medical professional at some later time can remove the prostatic stent 10 by simply pulling on the removal segment 45 or through endoscopic means.

Another embodiment of a prostatic stent 110 of the invention is shown in FIG. 8A. The prostatic stent 110 includes a first segment 120 with a plurality of openings or ports 115, a second segment 140, and a connecting segment 150 disposed between the first and second segments 120, 140. The first and second segments 120, 140 are tubular members that maintain the patient's urethra 3 open and able to pass bodily fluids, such as urine, from the bladder through the urethra 3. Both segments 120, 140 include lumens extending within each segment 120, 140 for facilitating drainage. In the disclosed embodiment, the first and second segments 120, 140 have a circular cross-sectional shape. The cross-sectional shape of the segments 120, 140 need not be circular, for example, the cross-sectional shape may be triangular, rectangular, elliptical, or even square.

The first segment 120 has a proximal portion 122, a distal end 124, an external surface 126, and an internal surface 128 defining the lumen of the first segment 120. When the stent 110 is properly positioned within the patient's urinary system 1, the first segment 120 is located substantially within the prostatic urethra with the proximal portion 122 located within the bladder 2 opening and the distal end 124 terminating prior to the proximal side of the external sphincter 4. To drain bodily fluids from the patient's bladder, the proximal portion contains at least one opening 132 in communication with the lumen of the first segment 120 and may contain an opening 134 sized to receive a guide wire. The external surface 126 of the first segment 120 contains the plurality of ports 115 for conveying an agent 160 to the external surface 126.

In one embodiment, the ports 115 may be in fluid communication with the lumen of the first segment 120 as shown in the cross-sectional view given in FIG. 8B. In this embodiment, the medical professional may apply an agent to the external surface 126 of the first segment 120 by inserting the agent into the lumen of the first segment 120. Once within the lumen, the agent may then flow through the ports 115 to the external surface 126.

Figure 8E:
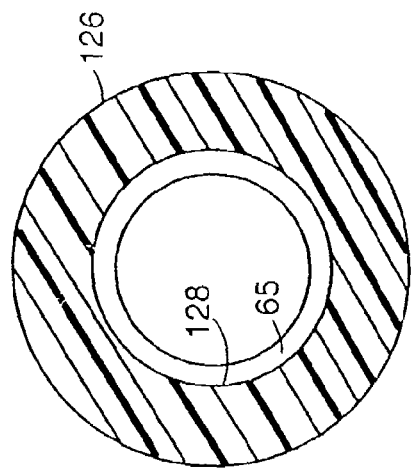
FIG. 8E is a cross-sectional view of the prostatic stent of FIG. 8C taken along line EE in FIG. 8A.
Figure 8D:
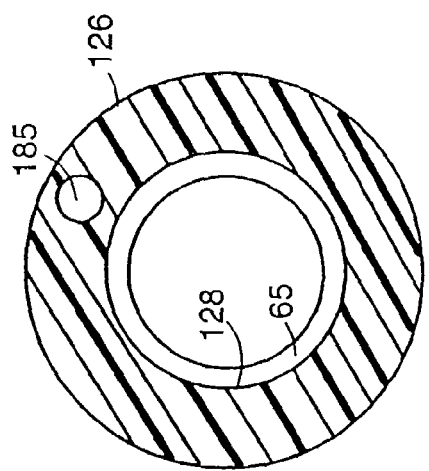
FIG. 8D is a cross-sectional view of the prostatic stent of FIG. 8C taken along line DD in FIG. 8A.

In another embodiment, shown in FIGS. 8C-8E, the ports 115 may be in fluid communication with a fluid channel 190 located between the external surface 126 and the internal surface 128 of the first segment 120. The fluid channel 190 extends within a region of the first segment 120 labeled F in FIG. 8A. FIG. 8C is a cross-sectional view of the first segment 120 taken along a line within this region, and FIGS. 8D and 8E are cross-sectional views taken along lines that are distal and proximal to this region, respectively. The medical professional may coat the external surface 126 by injection of the agent into an inlet channel 185 that extends from the distal end 124 of the first segment 120 to the fluid channel 190. After the medical professional injects the agent, the agent flows through the inlet channel 185, to the fluid channel 190, and then to the ports 115, which are in fluid communication with the external surface 126.

An agent, such as a hemostatic agent or other active agent(s), may be delivered to the ports 115 in vivo and then discharged to the external surface 126 of the first segment 120 during or after insertion of the prostatic stent 110 within the patient's urinary system 1. The number, location, and diameter of the ports 115 may be varied depending on the viscosity of the agent 160, the size of a tissue area to be treated, and the level of vasculature in the body tissue, high levels of which correlate with an increased risk of harm due to hemorrhaging. The ports 115 are preferably placed at intervals around the circumference of the first segment 120 in order to provide even and rapid delivery of the agent 160 to the tissue during and/or after insertion of the prostatic stent 110. In some embodiment, to prevent blood coagulation within the lumen of the first segment 140, the internal surface 148 may be coated with the anticoagulant agent 65 prior to insertion as shown in FIGS. 8C-8E.

Figure 8F:
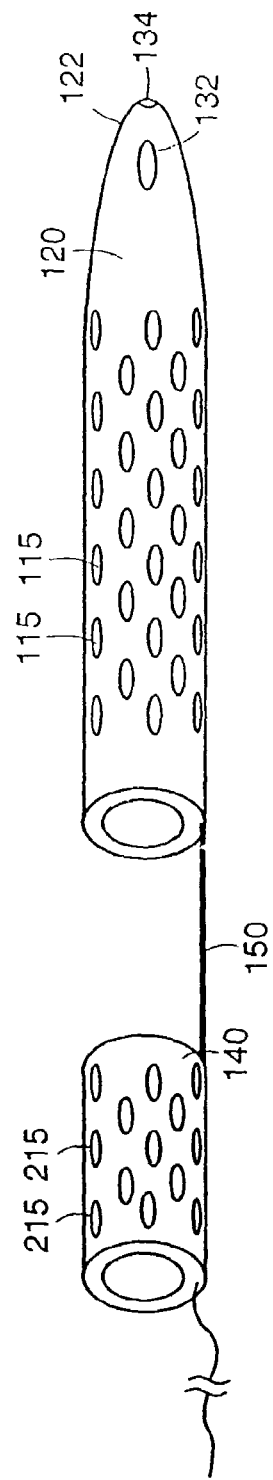
FIG. 8F is a perspective view of another embodiment of a prostatic stent.

The second segment 140 of the prostatic stent 110 includes a proximal end 142, a distal end 144, and external surface 146, and an internal surface 148. In the embodiment shown in FIG. 8A, the second segment 140 does not include a hemostatic agent nor does the second segment 140 have ports for conveying the agent 160 to the external surface 146 of the second segment 140. Alternatively, other embodiments of the invention may include these features if desired as shown in FIG. 8F. The second segment 140 can further include a removal segment 145 that can be used by a medical professional for positioning and removing the prostatic stent 110.

The connecting segment 150 extends between the first and second segments 120, 140 joining the first and second segments 120, 140 together. The connecting segment 150 is made from a thin biocompatible material that when located within the patient's body does not interfere with the normal operation of the external sphincter 4. In the disclosed embodiment, the connecting segment 150 is a stainless steel wire coated in silicone. The connecting member 150 may also be made from other biocompatible metals, such as titanium, or polymers, such as silicone, or even a suture.

Figure 9:
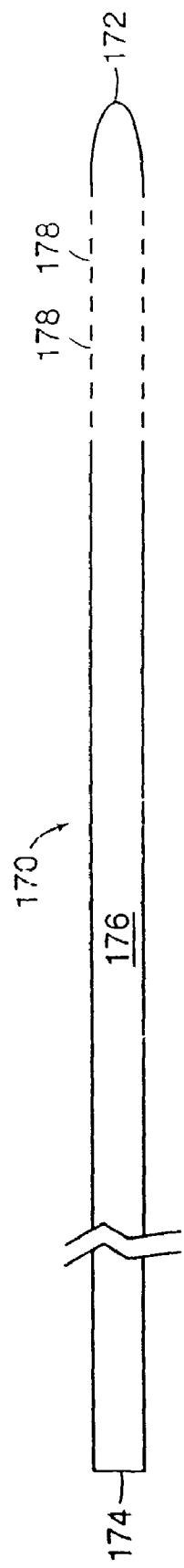
FIG. 9 is an enlarged side view of a stylet used to position the prostatic stent of FIG. 8A within the male urinary system.

In one embodiment, the medical professional inserting the prostatic stent 110 may use a stylet 170 to position the prostatic stent 110 as well as to convey a medical agent such as a hemostatic agent to the prostatic stent 110. Referring to FIGS. 9 and 10, the stylet comprises a proximal end 172, a distal end 174, a fluid channel 176, and a plurality of fluid ports 178 in fluid communication with the fluid channel 176. The medical professional connects the stylet 170 to the prostatic stent 110 by passing the proximal end 172 of the stylet 170 through the lumens of the second and first segments 140, 120 as shown in FIG. 11. Once the stylet 170 is within the prostatic stent 110, the medical professional aligns the ports 115 in the prostatic stent 110 with the ports 178 of the stylet 170, thereby creating a continuous open passageway for fluid to travel. Before inserting the stylet 170 with the connected and aligned prostatic stent 110 into the patient's urinary system 1, the medical professional connects an agent delivery mechanism 180, such as a syringe, to the distal end 174 of the stylet 170. Within a loading chamber 182 of the agent delivery mechanism 180 is the agent 160 that is to be delivered to the prostatic stent 110.

Figure 12:
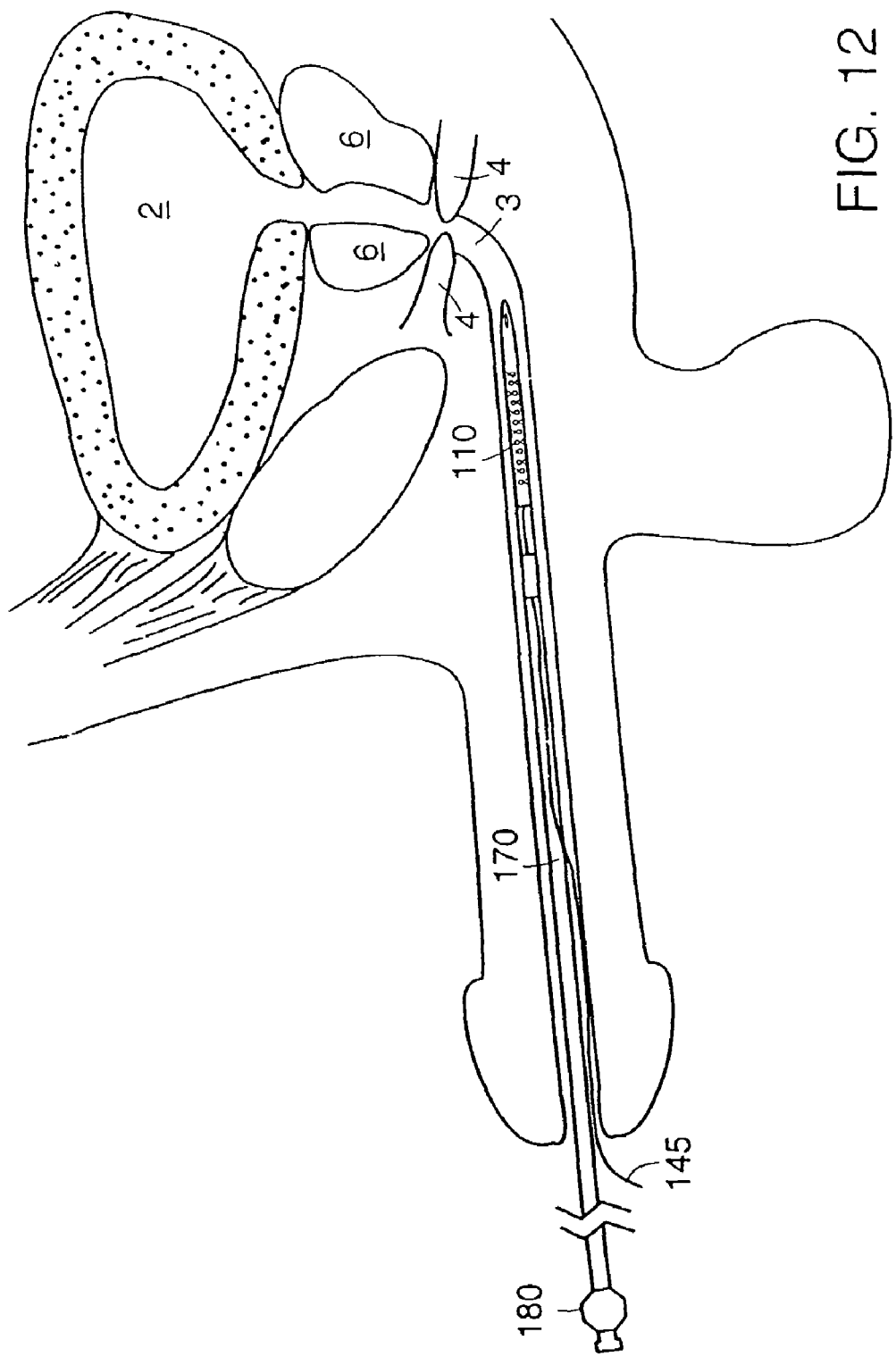
FIG. 12 is a schematic view showing the stylet and prostatic stent being inserted into the male urinary system.

The medical professional inserts the connected and aligned stylet 170 and prostatic stent 110 into the patient's urethra 3 as shown in FIG. 12. The medical professional then navigates the prostatic stent 110 through the patient's urethra 3 until the prostatic stent 110 is positioned such that the first segment 120 is located on the proximal side of the patient's external sphincter 4, the second segment 140 is located on the distal side of the external sphincter 4, and the connecting segment 150 extends between the first and second segments 120, 140.

Figure 13:
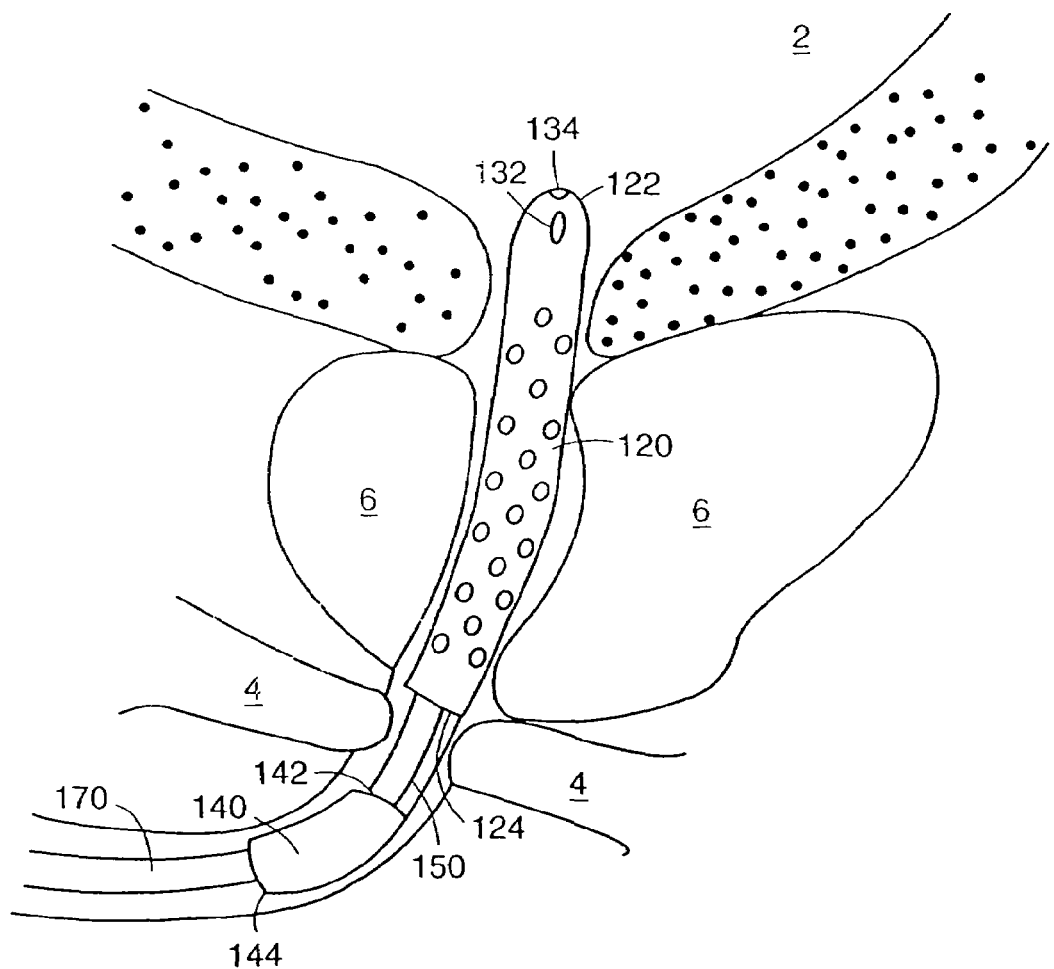
FIG. 13 is an enlarged schematic view of the stylet and prostatic stent during placement within the male urinary system.

The medical professional may discharge the agent 160 from the agent delivery mechanism 180 either during insertion or after the prostatic stent 110 is positioned within the patient's urinary system 1 as shown in FIG. 13. Once the medical professional has activated the agent delivery mechanism 180, the agent 160 within the agent delivery mechanism 180 passes through the distal end 174 of the stylet 170, travels through the fluid channel 176, and is delivered to the external surface 126 of the first segment 120 via the ports 178, 115. As previously described, the second segment 140 may also include ports 215 for conveying the agent 160. To deliver the agent 160 to the ports 215 in the second segment 140, the stylet 170 may include fluid ports 278 (FIG. 14A) similar to fluid ports 178 but located to communicate with the second segment 140 when the stylet 170 and the prostatic stent 110 are connected (FIG. 14B).

Figure 15:
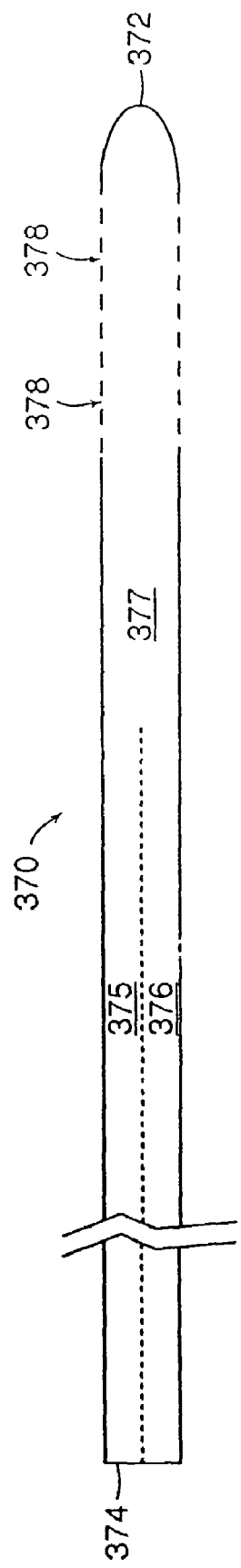
FIG. 15 is a side view of another embodiment of a stylet.

The agent 160 may be an antibiotic or other drug, or even one of the hemostatic agents described above. The agent 160 may also be a two component formulation comprising (1) a polymerizable agent such as for example a polymerizable hemostatic agent and (2) a polymerizing agent. Examples of polymerizing hemostatic agents include but are not limited to fibrinogen, alginate, and collagen. It may be desirable to keep the polymerizable agent and the polymerizing agent separate until the prostatic stent 110 is properly positioned within the patient's urinary system 1. In one embodiment, the prostatic stent 110 may be pre-coated with the polymerizable agent. To convert the polymerizable agent to the agent 160 in vivo, the medical professional discharges the polymerizing agent from the agent delivery mechanism 180. In another embodiment of the invention, the medical professional may simultaneously discharge the polymerizing and polymerizable agents to the prostatic stent 110. FIG. 15 shows one embodiment of a stylet 370 that can accommodate both the polymerizing and polymerizable agents. The stylet 370 has a proximal end 372, a distal end 374, a first fluid channel 375, a second fluid channel 376, a fluid mixing channel 377, and a plurality of ports 378 for conveying the agent 160 to the prostatic stent 110.

The first and second fluid channels 375, 376 are parallel to each other and extend from the distal end 374 of the stylet 370 to the fluid mixing channel 377. To coat the external surface 126 of the stent 110 with the agent 160, the medical professional discharges the polymerizable agent into the first fluid channel 375 and the polymerizing agent into the second fluid channel 376. The polymerizing and polymerizable agents mix together in the fluid mixing channel 377 forming the agent 160 that is to be delivered to the external surface 126 of the prostatic stent 110 via the ports 378, 115.

Figure 16:
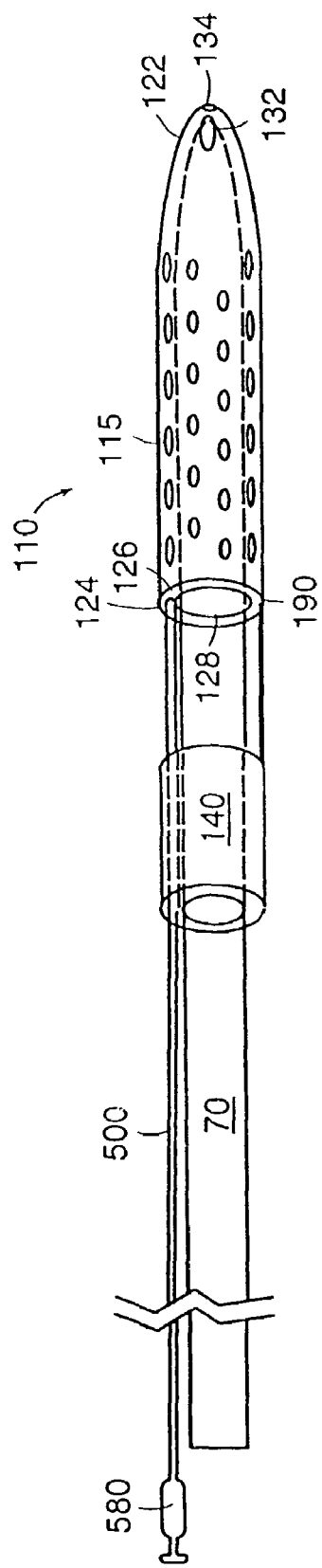
FIG. 16 is a perspective view of another embodiment of a prostatic stent connected to a stylet and a cannula.

Alternatively, the medical professional may use the stylet 70 to place the prostatic stent 110 and a cannula 500 (FIG. 16) to deliver the agent 160 to the prostatic stent 110 in vivo. The medical professional uses a similar procedure for connecting the prostatic stent 110 to the stylet 70 as previously described for the prostatic stent 10 and stylet 70. However, before the medical professional inserts the prostatic stent 110 and stylet 70 into the patient's urinary system 1, he or she inserts the cannula 500 into the inlet channel 185 (FIG. 8D) which is in fluid communication with the fluid channel 190 (FIG. 8C) of the prostatic stent 110. The medical professional navigates the prostatic stent 110 connected with the stylet 70 and cannula 500 through the patient's urinary system 1 until the prostatic stent 110 is properly positioned. The medical professional may discharge the agent 160 through the cannula 500, with a syringe 580 or some other delivery mechanism either during the insertion of the prostatic stent 110 or after the prostatic stent 110 has been properly positioned within the urinary system 1.

Figure 17:
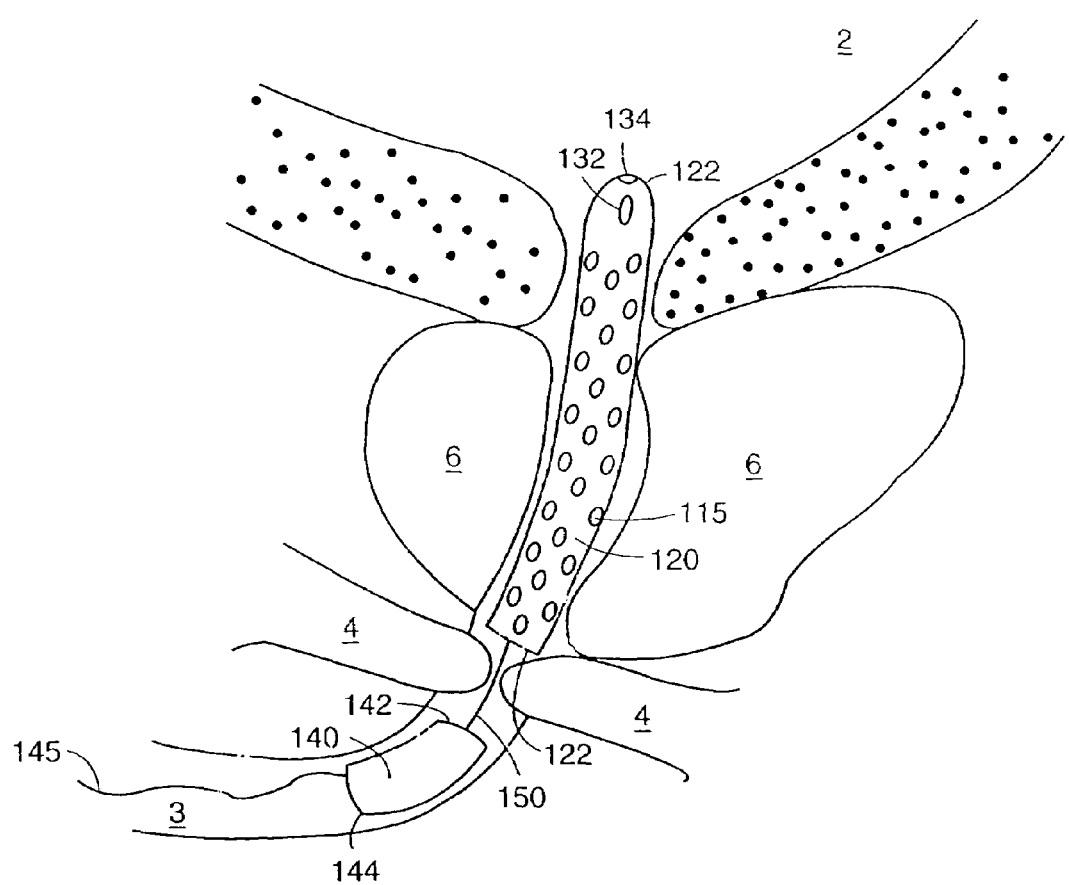
FIG. 17 is an enlarged schematic view of the prostatic stent of FIG. 8A positioned within the male urinary system.

Referring to FIG. 17, after confirming proper placement of the prostatic stent 110 and discharging the agent 160 to the prostatic stent 110, the medical professional removes the stylet 170, stylet 370, or stylet 70 and cannula 500 from the patient's urinary system 1, thereby leaving the prostatic stent 110 positioned within the patient's urinary system 1 and returning voluntary control of the external sphincter 4 to the patient. Any medical professional at some later time can remove the prostatic stent 110 by simply pulling on the removal segment 145 or through endoscopic means.

Variations, modifications, and other implementations of what is described herein will occur to those of ordinary skill in the art without departing from the spirit and the scope of the invention. The invention is not to be limited only to the preceding illustrative description.

What is claimed is:

1. A prostatic stent for use in a patient comprising:
    (a) a first segment locatable on the proximal side of the patient's external urinary sphincter and including an external surface, an internal surface, a proximal portion, a distal end, a lumen defined by the internal surface and extending within the first segment, and a plurality of ports disposed along substantially the entire length of the first segment, said plurality of ports in fluid communication with the lumen for applying at least one agent to the external surface from the lumen, the proximal portion including at least one opening in communication with the lumen for receiving fluid from the bladder of the patient, the distal end terminating on the proximal side of the external urinary sphincter when the prostatic stent is placed within the body of the patient;
    (b) a second segment locatable on the distal side of the external urinary sphincter of the patient and including an external surface, an internal surface, a proximal end, a distal end, and a lumen defined by the internal surface and extending within the second segment, the proximal end terminating on the distal side of the external urinary sphincter when the prostatic stent is placed within the body of the patient;
    (c) a wire disposed between the first and second segments and coupling together the first and second segments;
    (d) an anticoagulant disposed on the internal surface of the first segment; and
    (e) a removal segment extending from the second segment.

2. The stent according to claim 1 further comprising an anticoagulant on the internal surface of the second segment.

3. The stent according to claim 2 wherein the anticoagulant is selected from the group consisting of acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

4. The stent according to claim 1 further comprising a polymerizable agent on the external surface of the first segment.

5. The stent according to claim 4 wherein the polymerizable agent is a polymerizable hemostatic agent selected from the group consisting of fibrinogen, alginate, and collagen.

6. The stent according to claim 4 further comprising an anticoagulant on the internal surface of the second segment.

7. The stent according to claim 6 wherein the anticoagulant is selected from the group consisting of acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

8. The stent according to claim 1 wherein the distal end of the first segment defines a first surface, the proximal end of the second segment defines a second surface facing the first surface, and the connecting segment is attached to a portion of the first surface and a portion of the second surface.

9. The stent according to claim 1 wherein the connecting segment wire is a coated.

10. A prostatic stent for use in a patient comprising:
    (a) a first segment locatable on the proximal side of the patient's external urinary sphincter and including an external surface, an internal surface, a proximal portion, a distal end, a lumen defined by the internal surface and extending within the first segment, and a plurality of ports disposed along substantially the entire length of the first segment, said plurality of ports in fluid communication with the lumen for applying at least one agent to the external surface from the lumen, the proximal portion including at least one opening in communication with the lumen for receiving fluid from the bladder of the patient, the distal end terminating on the proximal side of the external urinary sphincter when the prostatic stent is placed within the body of the patient;
    (b) a second segment locatable on the distal side of the external urinary sphincter of the patient and including an external surface, an internal surface, a proximal end, a distal end, and a lumen defined by the internal surface and extending within the second segment, the proximal end terminating on the distal side of the external urinary sphincter when the prostatic stent is placed within the body of the patient;
    (c) a connecting segment disposed between the first and second segments and coupling together the first and second segments, the connecting segment being devoid of a lumen;
    (d) an anticoagulant disposed on the internal surface of the first segment; and
    (e) a removal segment extending from the second segment.

11. The stent according to claim 10 further comprising an anticoagulant on the internal surface of the second segment.

12. The stent according to claim 10 wherein the anticoagulant is selected from the group consisting of acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

13. The stent according to claim 10 further comprising a polymerizable agent on the external surface of the first segment.

14. The stent according to claim 10 wherein the polymerizable agent is a polymerizable hemostatic agent selected from the group consisting of fibrinogen, alginate, and collagen.

15. The stent according to claim 10 further comprising an anticoagulant on the internal surface of the second segment.

16. The stent according to claim 10 wherein the anticoagulant is selected from the group consisting of acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

17. The stent according to claim 10 wherein the connecting segment has a first end and a second end, the first end being connected to the distal end of the first segment and the second end being connected to the proximal end of the second segment.

18. The stent according to claim 10 wherein the distal end of the first segment defines a first surface, the proximal end of the second segment defines a second surface facing the first surface, and the connecting segment is attached to a portion of the first surface and a portion of the second surface.

19. The stent according to claim 10 wherein the connecting segment includes a wire.

* * * * *